United States Patent [19]
Yanagisawa

[11] Patent Number: 5,646,415
[45] Date of Patent: Jul. 8, 1997

[54] APPARATUS FOR DETECTING A DEFECT OF AN OPTICAL DISC BASED ON SENSOR OUTPUTS FOR ADJACENT POSITIONS

[75] Inventor: Yoshitake Yanagisawa, Shizuoka, Japan

[73] Assignee: Sony Disc Technology Inc., Kanagawa, Japan

[21] Appl. No.: 516,874

[22] Filed: Aug. 18, 1995

[30] Foreign Application Priority Data

Aug. 26, 1994 [JP] Japan ................................ 6-202374

[51] Int. Cl.$^6$ ................................................ G01N 21/86
[52] U.S. Cl. ........................... 250/559.45; 250/559.39; 356/430
[58] Field of Search .................... 250/559.45, 559.46, 250/559.41, 559.48, 559.49, 559.39, 559.18; 356/237, 240, 430, 431; 369/58, 54, 82

[56] References Cited

U.S. PATENT DOCUMENTS

| | | | |
|---|---|---|---|
| 4,508,450 | 4/1985 | Ohshima et al. | 250/559.45 |
| 4,794,265 | 12/1988 | Quackenbos et al. | 250/559.45 |
| 4,950,911 | 8/1990 | Williams et al. | 250/559.45 |

*Primary Examiner*—Que Le
*Attorney, Agent, or Firm*—Jay H. Maioli

[57] ABSTRACT

A disc defect inspection apparatus which can detect a defect of a disc, such as an optical disc, with high accuracy. A disc defect inspection apparatus includes a rotating portion for rotating a disc laser radiating optical portion for radiating laser lights on the disc rotated by the rotating portion under predetermined scanning conditions, sensors for detecting reflected laser lights from the disc, and a memory in which output signals of the sensors are stored together with address data generated in unison with the scanning of laser lights. Sensor outputs indicative of address positions of the disc are stored in the memory and sensor outputs near the address positions are read out and a defect of the disc is detected on the basis of a spatial difference among the nearby sensor outputs and the sensor output of the center address position.

5 Claims, 7 Drawing Sheets

APPARATUS FOR DETECTING A DEFECT OF AN OPTICAL DISC BASED ON SENSOR OUTPUTS FOR ADJACENT POSITIONS

BACKGROUND OF THE INVENTION

The present invention relates to a disc defect inspection apparatus for use in inspecting a defect of a disc, such as an optical disc or a magneto-optical disc in and from which data is recorded and reproduced optically.

When optical discs in and from which data is optically recorded and reproduced by laser light are manufactured, the manufactured optical discs are inspected in order to see whether a signal recording surface or a disc surface is formed in the predetermined state (i.e., the signal recording surface or the disc surface is smooth). When the optical disc is inspected, laser light is radiated on the signal recording surface of the optical disc, for example, and an intensity of reflected light of the laser light is detected. If the intensity of reflected light exceeds a predetermined amount, then it is determined that the signal recording surface has a certain defect.

According to the above-mentioned method of inspecting a defect of an optical disc by detecting an intensity of reflected light, a defect of the optical disc can be detected, however, the state in which a defect has occurred in the optical disc cannot be specified closely. Specifically, even though some defects, such as irregularities formed on the signal recording surface of the optical disc can be judged according to the above-mentioned method, types of irregularities, i.e., concavities or convexities cannot be specified. Moreover, heights of convexities or depths of concavities cannot be detected.

On the other hand, there are known some different types of defects (unevenness on the disc surface) wherein a shape of a beam spot is distorted even though an intensity of reflected light is not changed substantially. These types of defect cannot be detected.

Concavities and convexities formed on the disc surface can be detected by increasing a sensitivity at which an intensity of reflected light is detected (i.e., defect can be judged on the basis of a very small change of an intensity of reflected light). However, if the detection sensitivity increases as described above, then a smudged disc surface may be determined as a defect of the disc. There is then the risk that a good disc will be erroneously determined as a defective disc.

To solve the aforesaid problem, the following method is proposed. All data that are recorded on one disc, for example, are previously stored in a memory. All data read out from an inspected disc are compared with the data stored in the memory one after another, thereby making it possible to completely inspect each inspected disc. However, when the above-mentioned inspection is carried out, an inspection apparatus needs a memory having a large storage capacity. Furthermore, the inspection requires a lot of time and is not suitable in actual practice.

SUMMARY OF THE INVENTION

In view of the aforesaid aspects, it is an object of the present invention to provide a disc defect inspection apparatus having a simple arrangement which can detect a defect of a disc such as an optical disc with high accuracy.

According to an aspect of the present invention, there is provided an apparatus for inspecting a defect of a disc which is comprised of rotating means for rotating the disc, laser radiating optical means for radiating laser light on the disc rotated by the rotating means under a predetermined scanning state, sensors for detecting reflected laser lights from the disc, and a memory in which output signals of the sensors are written together with address data generated in unison with scanning of the laser light, wherein sensor outputs indicative of disc address positions written in the memory and sensor outputs indicative of nearby positions are read out from the memory and a defect is detected on the basis of a difference between the sensor output of the nearby positions and sensor output of the reference address position.

DETAILED DESCRIPTION OF THE PREFERRED EMBODIMENT

An inspection apparatus for inspecting a defect of a disc according to an embodiment of the present invention will now be described with reference to the drawings.

Figure 1:
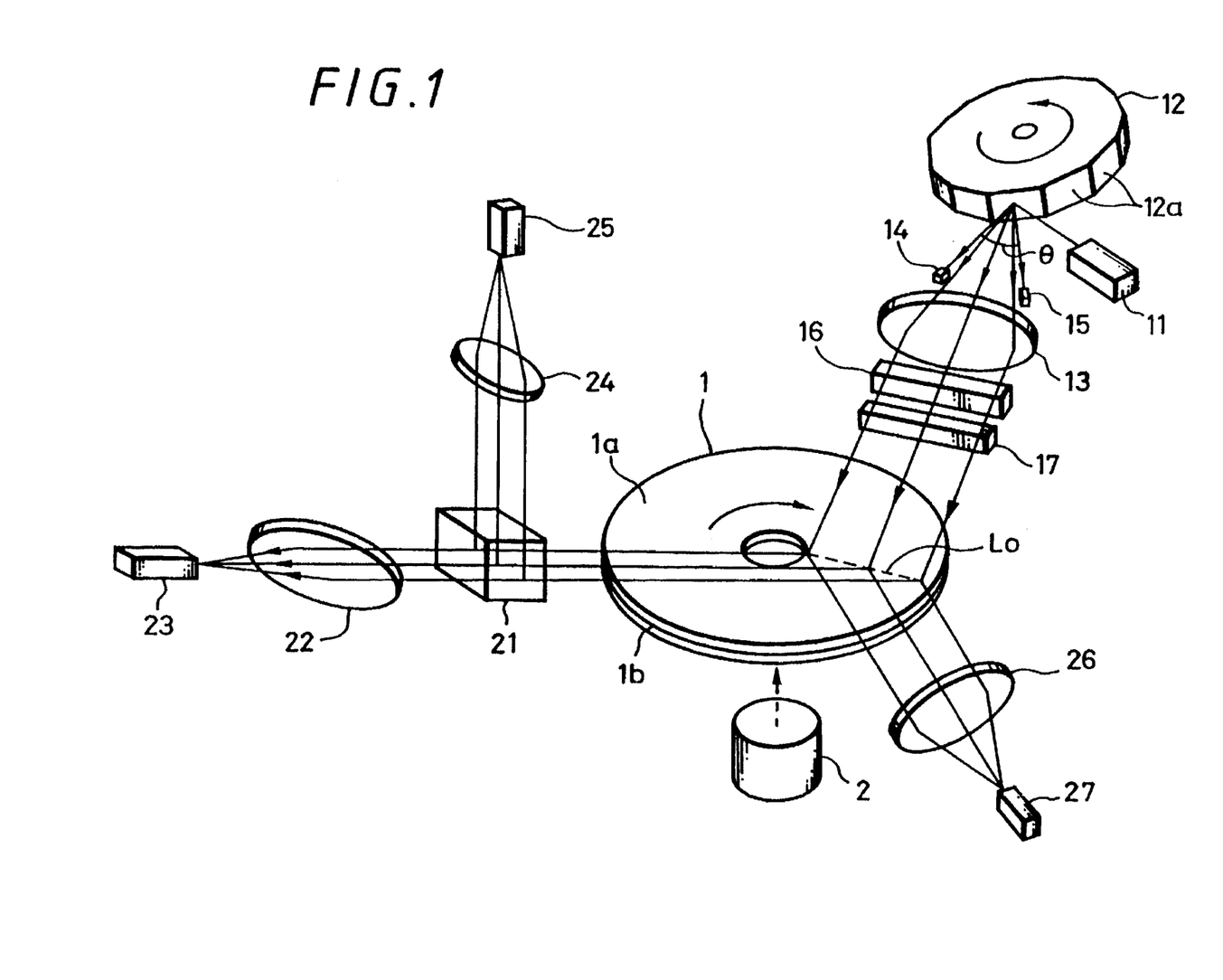
FIG. 1 is a perspective view showing an arrangement of an optical system of an apparatus for inspecting a defect of a disc according to an embodiment of the present invention.

FIG. 1 shows a perspective view of an arrangement of an optical system of an inspection apparatus for inspecting a defect of a disc according to an embodiment of the present invention.

As shown in FIG. 1, there is provided an optical disc 1 as an inspected object. The optical disc 1 is made of a transparent resin and is composed of an upper disc surface 1a, and a signal recording surface 1b formed of a suitable material, such as a metal film and a lower disc surface 1c. The signal recording surface 1b is formed inside the optical disc 1 sandwiched between the upper disc surface 1a and the lower disc surface 1c. When laser light is radiated on the "disc 1, because the disc 1 is made of transparent material, the light is able to pass through the upper disc surface 1a and radiate on the signal recording surface 1b, so that data that has been recorded on the signal recorded surface 1b in the form of pits is reproduced from the optical disc 1. The inspection apparatus for inspecting a defect of a disc according to this embodiment is adapted to inspect a defect of the optical disc 1. The optical disc 1 is rotated by a spindle motor 2. A laser light source 11 is formed of a suitable laser device, such as a semiconductor laser. Laser light for inspecting a defect of a disc is emitted from the laser light source 11 and radiated on the signal recording surface 1b of the optical disc 1.

According to this embodiment, laser light emitted from the laser light source 11 is reflected by a rotary mirror 12. The rotary mirror 12 is often referred to as a polygon mirror. The polygon mirror 12 is composed of a plurality of plane mirrors 12a attached on the side surface thereof at a predetermined interval. When the polygon mirror 12 is rotated at a constant speed by a suitable rotating means (not shown), reflected light from each plane mirror 12a is distributed with a predetermined angle θ. Light-receiving sensors 14, 15 are disposed at the positions whereat the light-receiving sensors 14, 15 can receive reflected light distributed to the innermost peripheral side and reflected light distributed to the outermost peripheral side of the optical disc 1, respectively. The light-receiving sensors 14, 15 are adapted to detect the scanning state of laser light.

A collimator lens 13 is disposed at the position whereat it can receive reflected light thus distributed with the predetermined angle θ. The collimator lens 13 collimates reflected laser light to provide parallel scanning laser light. Then, the parallel scanning laser light is changed to circularly polarized light by a beam splitter 16 and a quarter waveplate 17. The parallel scanning laser light of circularly polarized light is radiated on the optical disc 1 at a predetermined angle. At that time, as shown in FIG. 1, incident positions of the parallel scanning laser light of circular polarized light are changed along the radial direction (direction shown by a dotted arrow $L_o$ on the optical disc 1) of the optical disc 1.

Laser light from the laser light source 11 is introduced from the disc surface 1a of the optical disc 1 and reflected on the signal recording surface 1b. The reflected laser light is classified as directly-reflected laser light and diffraction reflected laser light. Initially, the directly-reflected laser light will be described.

Parallel scanning laser light that has been directly reflected on the signal recording surface 1b of the optical disc 1 is introduced into a polarization beam splitter 21. A condenser lens 22 converges laser light passed through the polarization beam splitter 21. A first light-receiving sensor 23 is disposed at the position (i.e., focus position of the condenser lens 22) whereat the laser light passed through the polarization beam splitter 21 and was converged by the condenser lens 22. The first light-receiving sensor 23 might be a sensor which can detect an intensity of received light and a position of received light.

Light reflected on the polarization beam splitter 21 is converged by a condenser lens 24. A second light-receiving sensor 25 is disposed at the position whereat the light reflected on the polarization beam splitter 21 is focused.

Diffraction reflected light reflected on the signal recording surface 1b of the optical disc 1 is converged by a condenser lens 26. A third light-receiving sensor 27 is disposed at the position whereat the diffraction reflected light is focused by the condenser lens 26. Each of the first, second and third light-receiving sensors 23, 25, 27 can obtain a detected output corresponding to an intensity of received laser light.

Figure 2:
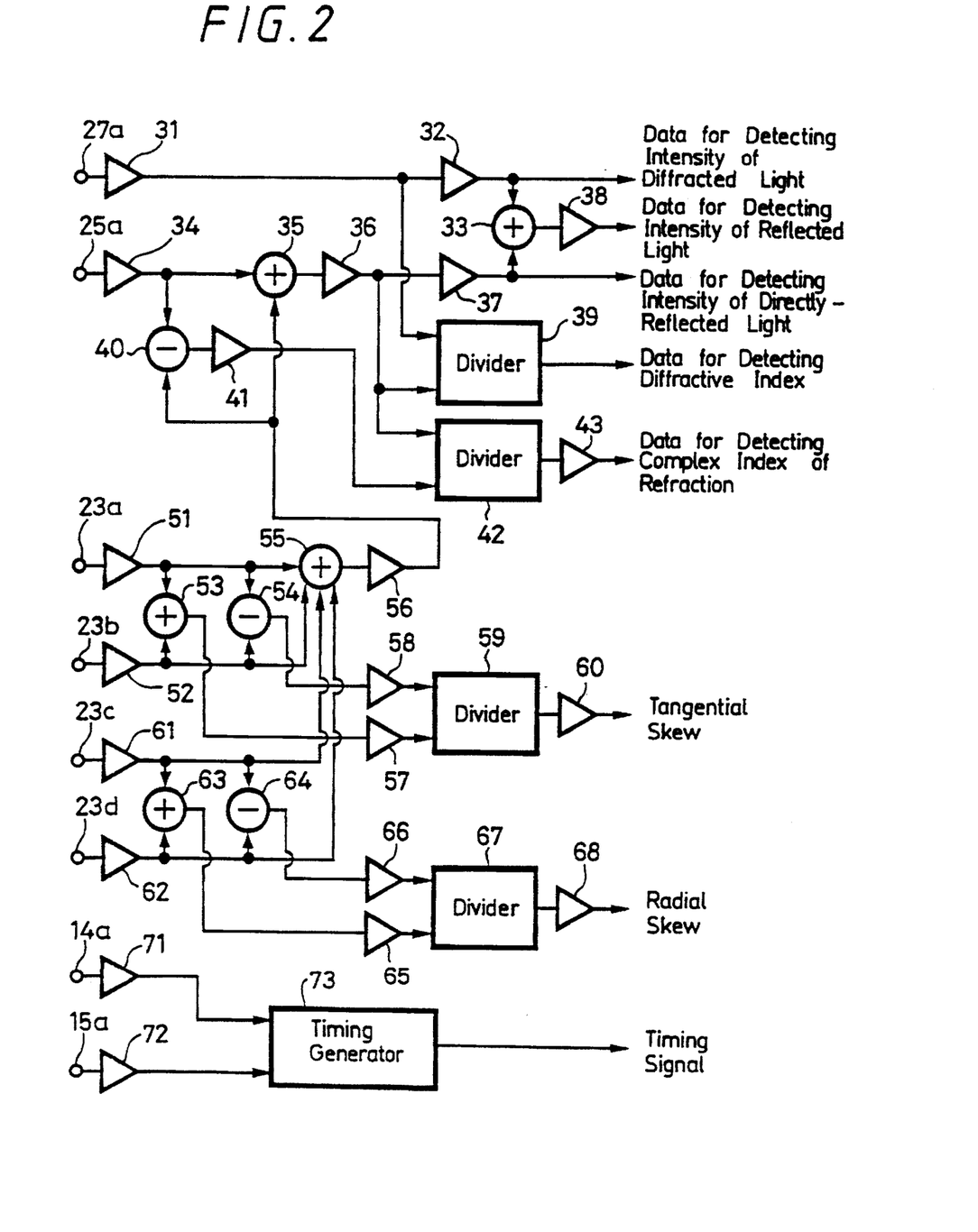
FIG. 2 is a diagram showing a circuit arrangement of a processing circuit for processing outputs of respective sensors according to the embodiment of the present invention.

A circuit arrangement for processing the detected output from each of the first, second and third light-receiving sensors 23, 25, 27 will be described with reference to FIG. 2.

A detected signal output from the third light-receiving sensor 27 is supplied through a terminal 27a to an amplifier 31. Art amplifier 32 is connected to the latter part of the amplifier 31. An amplified output from the amplifier 32 is output as data for detecting an intensity of diffracted light.

A detected signal output from the second light-receiving sensor 25 is supplied from a terminal 25a to an amplifier 34.

An amplified output from the amplifier 34 is supplied to an adder 35. The adder 35 adds the output of the amplifier 34 and an output of an amplifier 56 which will be described later on. The output of the first amplifier 56 can be obtained in the output of the amplifier 56. An added output from the adder 35 is supplied through amplifiers 36, 37 and output as data for detecting an intensity of directly-reflected light.

An adder 33 adds the outputs of the amplifier 32 and the amplifier 37. An added output from the adder 33 is output through an amplifier 38 as data for detecting an intensity of reflected light.

A divider 39 divides the outputs of the amplifiers 31 and 36. A divided output from the divider 39 is used as data for detecting a diffractive index.

The output of the amplifier 34 and an output of the amplifier 56, which will be described later on, are supplied to a subtractor 40. The subtractor 40 subtracts the two outputs supplied thereto from the amplifiers 34 and 56 to provide a difference between the two outputs. A subtracted output from the subtractor 40 is supplied through an amplifier 41 to a divider 42. The output of the amplifier 36 is supplied to the divider 42 and the divider 42 divides the two outputs supplied thereto from the subtractor 40 and the amplifier 36 to provide a divided output. The divided output from the divider 42 is output through an amplifier 43 as data for detecting a complex index of refraction.

Four sensor outputs from the first light-receiving sensor 23 are supplied to terminals 23a, 23b, 23c, 23d, respectively. The sensor outputs supplied to the terminals 23a and 23b are data indicative of the position of the circumferential direction of the optical disc 1. The sensor outputs supplied to the terminals 23c and 23d are data indicative of the position of the radial direction of the optical disc 1. The respective outputs obtained at the terminals 23a, 23b, 23c, 23d are supplied through amplifiers 51, 52, 61, 62, respectively to an adder 55 and thereby are added. The adder 55 supplies an added output through the amplifier 56 to the adder 35 and the subtractor 40 and thereby used to form detecting data, such as data for detecting an intensity of reflected laser light.

The outputs obtained at the terminals 23a, 23b are supplied through the amplifiers 51, 52 respectively to an adder 53 and thereby added. The adder 53 supplies the added output through an amplifier 57 to a divider 59. The outputs of the amplifiers 51, 52 are supplied to a subtractor 54 and a subtracted output from the subtractor 54 is supplied through an amplifier 58 to the divider 59. The divider 59 divides the outputs of the amplifiers 57, 58 and outputs a divided output through an amplifier 60. The divided output of the divider 59 is used as data for detecting a tangential skew.

The outputs supplied to the terminals 23c, 23d are supplied through the amplifiers 61, 62 respectively to an adder 63 and thereby added. The adder 63 supplies an added output through an amplifier 65 to a divider 67. The outputs of the amplifiers 61, 62 are supplied to a subtractor 64 and a subtracted output of the subtractor 64 is supplied through an amplifier 66 to the divider 67. Then, the divider 67 divides the outputs of the amplifiers 65, 66 and outputs a divided output through an amplifier 68 as data for detecting a radial skew.

The outputs from the light-receiving sensors 14 and 15 which detect the scanning states of laser lights distributed by the polygon mirror 12 are supplied from terminals 14a and 15a respectively through amplifiers 71 and 72, respectively to a timing generator 73. In response to the outputs supplied thereto from the light-receiving sensors 14, 15, the timing generator 73 therefore generates a timing signal which is in unison with the period of the scanning state of laser light.

An arrangement of a defect portion detecting unit which detects a defect portion by using detecting data generated from the outputs of the light-receiving sensors will be described with reference to FIG. 3.

Figure 3:
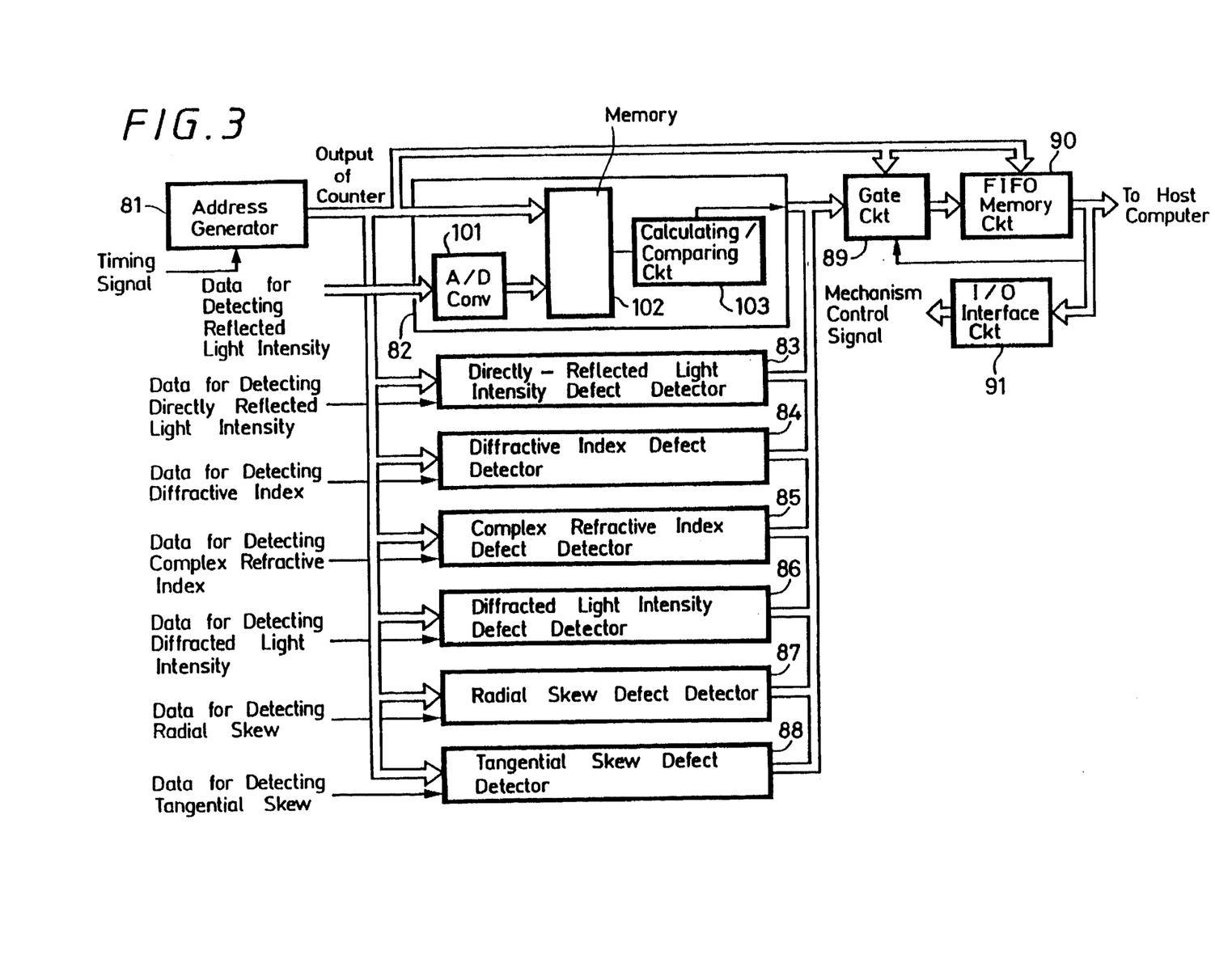
FIG. 3 is a block diagram showing an arrangement of a defective portion detecting unit according to the embodiment of the present invention.

In FIG. 3, an address generator 81 includes a counter (not shown) and is supplied with the timing signal which is obtained from the timing generator 73 on the basis of the outputs from the light-receiving sensors 14 and 15. The counter of the address generator 81 is reset in synchronism with the above-mentioned timing signal. The address generator 81 outputs an output of the counter as an address signal.

The address signal output from the address generator 81 is supplied to defect detectors 82, 83, . . . , 88. The defect detectors 82, 83, . . . , 88 are of the same circuit arrangement but are supplied with different detecting data to thereby detect defects on the basis of detecting data supplied thereto. Specifically, as shown in FIG. 3, the defect portion detecting unit is composed of a reflected light intensity defect detector 82 supplied with data for detecting an intensity of reflected light, a directly-reflected light intensity defect detector 83 supplied with data for detecting an intensity of directly-reflected light, a diffractive index defect detector 84 supplied with data for detecting a diffractive index, a complex refractive index defect detector 85 supplied with data for detecting a complex refractive index, a diffracted light intensity defect detector 86 supplied with data for detecting an intensity of diffracted light, a radial skew defect detector 87 supplied with data for detecting a radial skew and a tangential skew defect detector 88 supplied with data for detecting a tangential skew.

Each of the defect detectors 82 through 88 includes an analog-to-digital (A/D) converter 101 for converting detected data into digital data, a memory 102 for storing therein the converted detected data together with address data and a calculating/comparing circuit 103 for judging a defect portion by calculating data stored in the memory 102. In this case, the memory 102 includes a relatively small storage capacity. Detected data which results from scanning the optical disc 1 by laser light along the radial direction of the optical disc 1 is stored in memory 102.

Figure 4:
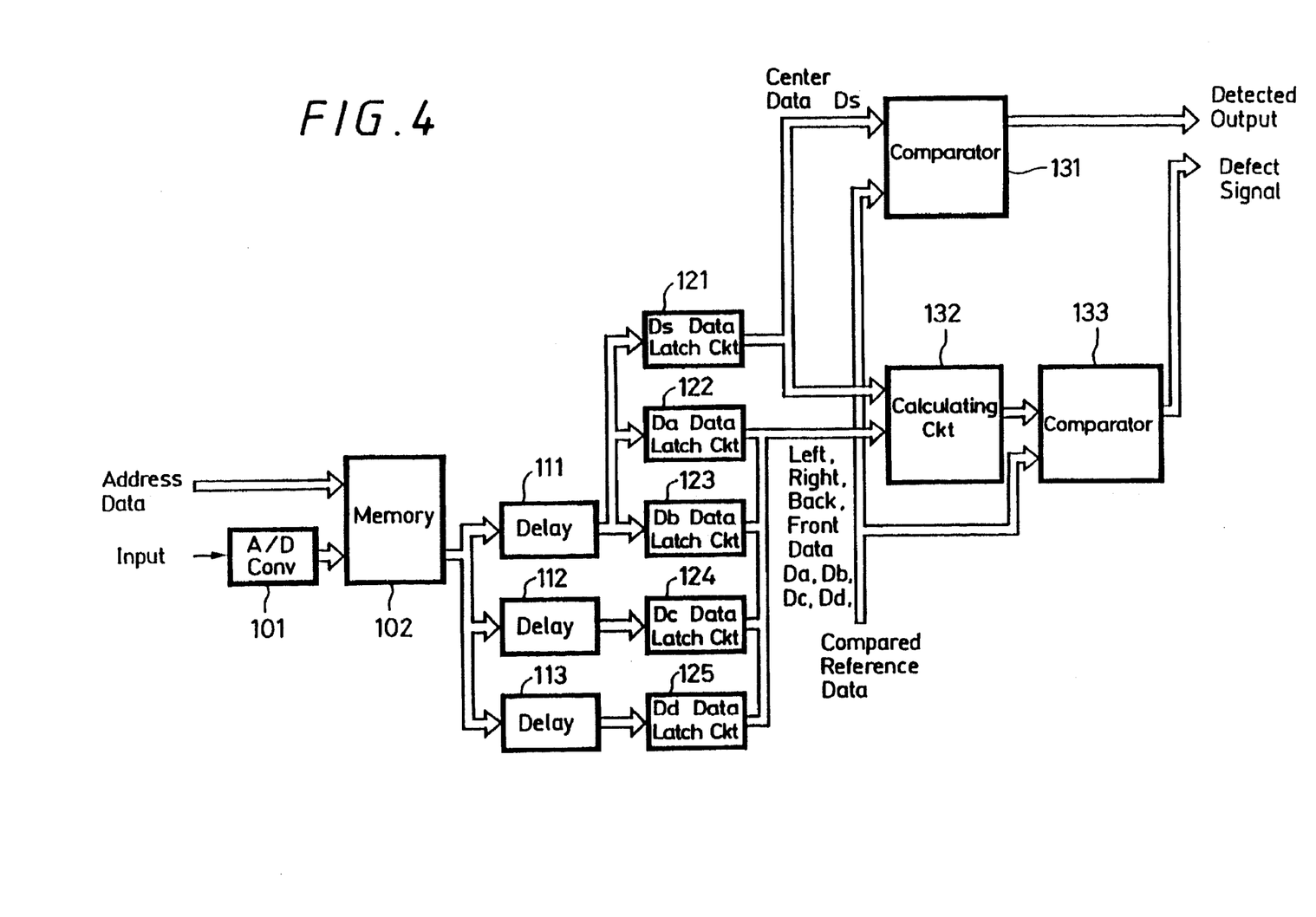
FIG. 4 is a block diagram showing in detail an arrangement of a calculating/comparing circuit used in the defective portion detecting unit shown in FIG. 3.

FIG. 4 shows in detail a circuit arrangement of the calculating/comparing circuit 103 provided in each of the defect detectors 82 through 88. As shown in FIG. 4, detected data stored in the memory 102 are read out in the order of addresses and supplied to delay circuits 111, 112, 113. Data are written in and read out from the memory 102 according to this embodiment on the basis of timing relations shown in FIGS. 5A to 5C.

Figure 5A:
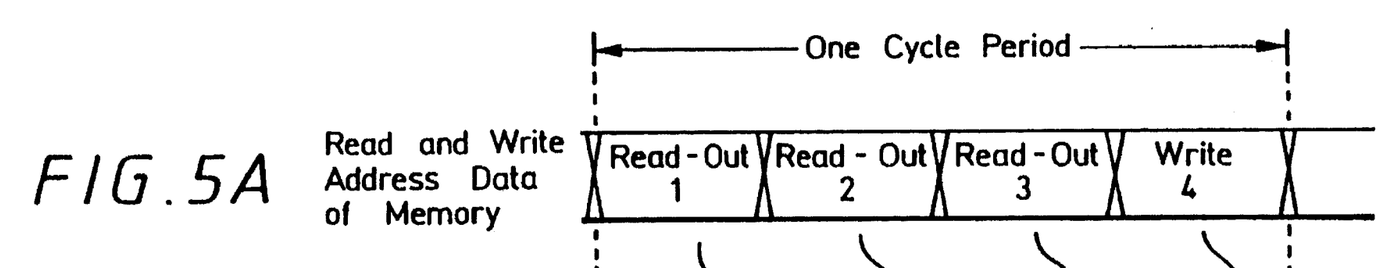
FIGS. 5A to 5C are timing charts showing the states that data is written in and read out from a memory according to the embodiment of the present invention.
Figure 5B:
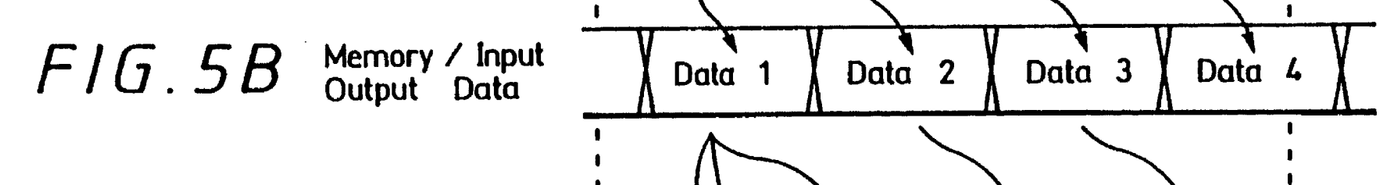

As shown in FIG. 5A, one cycle period is divided into four periods wherein data are read out three times from the memory 102 and data are written once in the memory 102 during one cycle period. Data that are written in the memory 102 once are detected data and address data. Data that are read out from the memory 102 three times during one cycle period will be described below. In the first read-out period, detected data (data 1 shown in FIG. 5B) of a predetermined read address (this read address changes by one address in each cycle) of a predetermined scanning line is read out from the memory 102. In the second read-out period, detected data (data 2 shown in FIG. 5B) of the same address of a scanning line which precedes by one line (or two lines) the scanning line read-out in the first read-out period is read out from the memory 102. In the third read-out period, detected data (data 3 shown in FIG. 5B) of the same address of a scanning line which succeeds by one line (or two lines) the scanning line read-out in the first read-out period is read out from the memory 102. Data that are written in the memory 102 during the write period behind the three read-out periods is data 4 shown in FIG. 5B.

Detected data read out from the memory 102 during the first period of one cycle period is supplied through the delay circuit 111 to data latch circuits 121, 122, 123. Latch timings of the above-mentioned three data latch circuits 121, 122, 123 are shifted slightly. Taking the latch timing of the data latch circuit 121 as a reference latch timing, the latch timing of the data latch circuit 122 is advanced a little from that of the data latch circuit 121 and the latch timing of the data latch circuit 123 is delayed a little from the data of the data latch circuit 121. Detected data read out from the memory 102 during the second period of one cycle period is supplied through the delay circuit 112 to a data latch circuit 124. Detected data read out from the memory 102 during the third period of one cycle period is supplied through the delay circuit 113 to a data latch circuit 125.

Figure 5C:
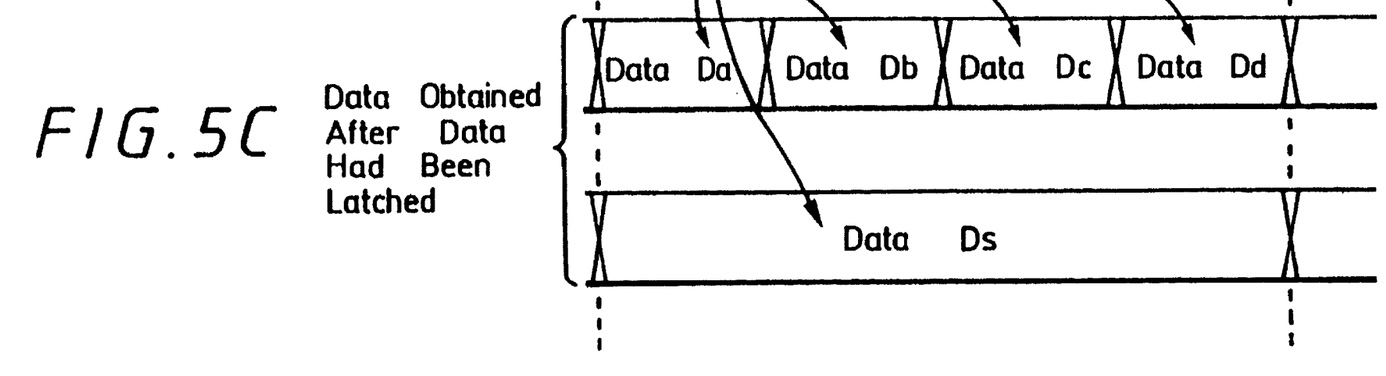

Let it be assumed that Ds is data latched by the latch circuit 121, Da is data latched by the data latch circuit 122, Db is data latched by the data latch circuit 123, Dc is data latched by the data latch circuit 124 and that Dd is data latched by the data latch circuit 125, respectively. The data Ds, Da, Db, Dc, Dd will be described more in detail below with reference to FIG. 5C. As shown in FIG. 5C, the data Ds, Da and Db are data obtained from the detected data read out from the memory 102 during the first period of one cycle period, the data Dc is data obtained from the detected data read out from the memory 102 during the second period of one cycle period and the data Dd is data obtained from the detected data read out from the memory 102 during the third period of one cycle period.

Figure 6:
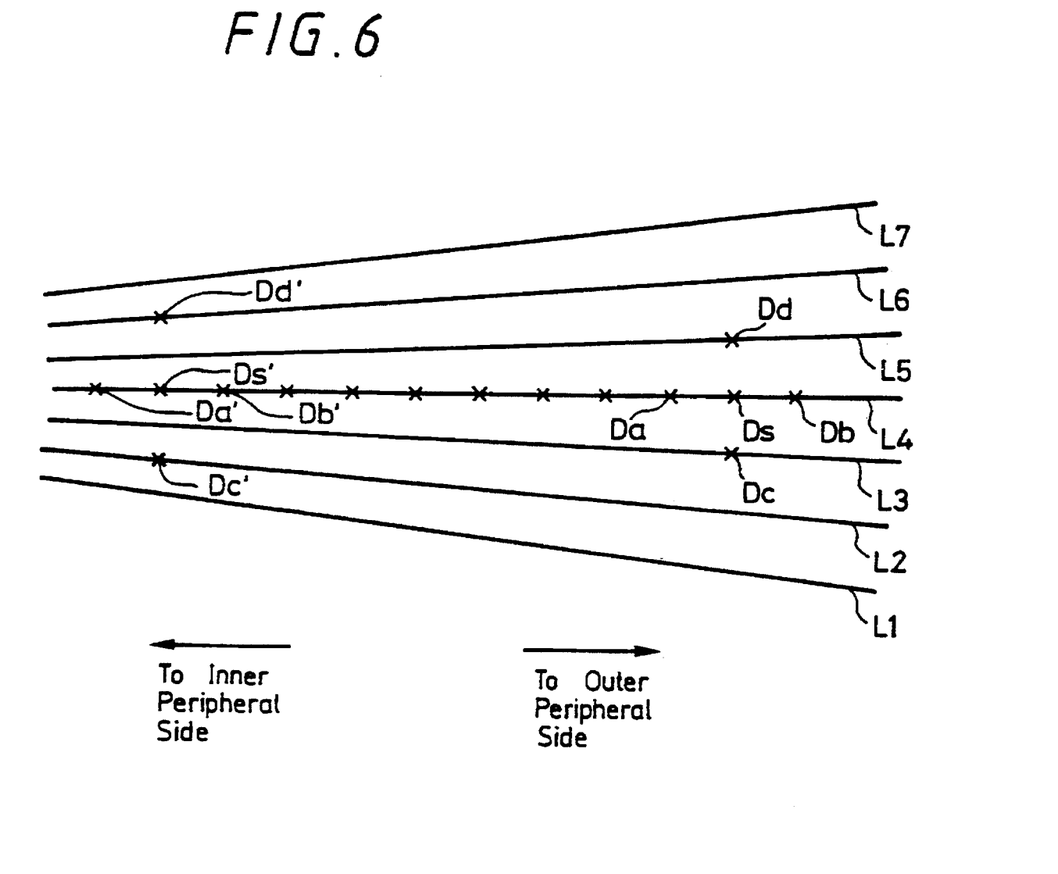
FIG. 6 is a diagram used to explain the sampled states of data on the disc.

Therefore, the data Ds, Da, Db, Dc, Dd respectively latched in the data latch circuits 121 to 125 become data that are spatially located in the state shown in FIG. 6. Specifically, let it be assumed that scanning lines L1, L2, L3, . . . , are formed by scanning the optical disc 1 by laser light along the radial direction of the optical disc 1 as shown in FIG. 6. Also, let it be assumed that sampling timings at which the A/D converter 101 samples detected data on the scanning line L4 are represented by crosses in FIG. 6. Then, when a certain data Ds on the scanning line L4 is latched by the data latch circuit 121, data Da located on the same scanning line L4 and which precedes the data Ds by one sample is latched by the data latch circuit 122. Also, data Db located on the same scanning line L4 and which succeeds the data Ds by one sample is latched by the data latch circuit 123. Further, data Dc located on the same address as that of the data Ds located on the scanning line L3 preceding the scanning line L4 by one line is latched by the data latch circuit 124. Furthermore, data Dd located on the same address as that of the data Ds located on the scanning line L5 succeeding the scanning line L4 by one line is latched by the data latch circuit 125.

Therefore, the data Da, Db, Dc, Dd located left, right, back and front, respectively of the data Ds are latched simultaneously.

In this embodiment, when data located near the inner peripheral side of the optical disc 1 are read out, data (data 2, 3 shown in FIG. 5B) on the scanning lines before and after the reference scanning line are read out from the memory 102 and data located on the scanning lines which precede and succeed the reference scanning line by two lines are latched by the data latch circuits 124, 125. With this arrangement, as shown in the portion near the inner peripheral side of the optical disc 1, when data Ds' located on the portion near the inner periphery of the optical disc 1 is read out from the memory 102 and latched by the data latch circuit 121, data Dc' latched by the data latch circuit 124 becomes data located on the same address of the scanning line L2 which precedes the scanning line L4 of data Ds' by two lines. Also, data Dd' latched by the data latch circuit 125 becomes data located on the same address of the scanning line L6 which succeeds the scanning line L4 of the data Ds' by two lines. Data Da' and Db' latched by the data latch circuits 122, 123, respectively become data located on the same scanning line L4 and which precedes and succeeds the data Ds' by one sample each similarly to the data Da and Db located at the portions near the outer peripheral side of the optical disc 1.

As described above, if the number of preceding and succeeding scanning lines is changed in the outer and inner peripheral sides of the optical disc 1, then it becomes possible to make distances of front, rear, left and right data with respect to the reference data Ds, Ds' become substantially the same. Specifically, when data of the same preceding and succeeding scanning lines of the outer and inner peripheral sides of the optical disc are latched, each spacing between the scanning lines is narrowed on the inner peripheral side of the optical disc so that a distance between data of preceding and succeeding scanning lines is unavoidably reduced. According to this embodiment, however, if the lines of data latched are changed on the outer and inner peripheral sides of the optical disc as described above, then it is possible to obtain data located at front, rear, left and right positions of the reference data with substantially the same distance from the reference data.

When the preceding and succeeding scanning lines of data latched on the outer and inner peripheral sides of the optical disc 1 (i.e., preceding and succeeding scanning lines of data read out from the memory 102) are switched, if the address of the reference data Ds read out from the memory 102, for example, is located at the address near the inner peripheral side of the optical disc 1 as compared with a predetermined address, then data located on the scanning lines which precedes or succeeds the scanning line of the reference data may be read out from the memory 102.

According to this embodiment, a defect of the optical disc 1 can be detected by using respective data and data located at the front, back, left and right positions of the reference data. Referring back to FIG. 4, the circuit arrangement for detecting a defect of the optical disc 1 will be described below.

As shown in FIG. 4, the center (reference) data Ds latched by the data latch circuit 121 is supplied to a comparator 131, wherein it is compared with comparison reference data supplied thereto from a host computer (not shown) of this disc defect inspection apparatus. If it is determined by the comparator 131 that the data Ds do not agree with the reference data, then the defect portion detecting unit determines that a corresponding address position is not correct and outputs a defect detected signal.

Then, the center data Ds and the peripheral data Da, Db, Dc, Dd latched by the data latch circuits 122 to 125, respectively are supplied to a calculating circuit 132 which calculates spatial differences among the peripheral data Da, Db, Dc, Dd and the center data Ds. At that time, a calculation expressed by the following equation (1) is carried out:

$$|Ds-Da|+|Ds-Db|+|Ds-Dc|+|Ds-Dd| \quad (1)$$

When the spatial differences among the center detected data and the peripheral detected data are calculated as described above, there is formed a spatial differentiating circuit. A spatial differentiated value calculated by the calculating circuit 132 is supplied to a comparator 133, wherein it is compared with comparison reference data supplied thereto from the host computer (not shown) of this disc defect inspection apparatus. If it is determined by the comparator 133 that the compared data do not agree with the comparison reference data supplied from the host computer of this disc defect inspection apparatus, then the defect portion detecting unit determines that the corresponding address position is not correct and outputs a defect detected signal.

Figure 7:
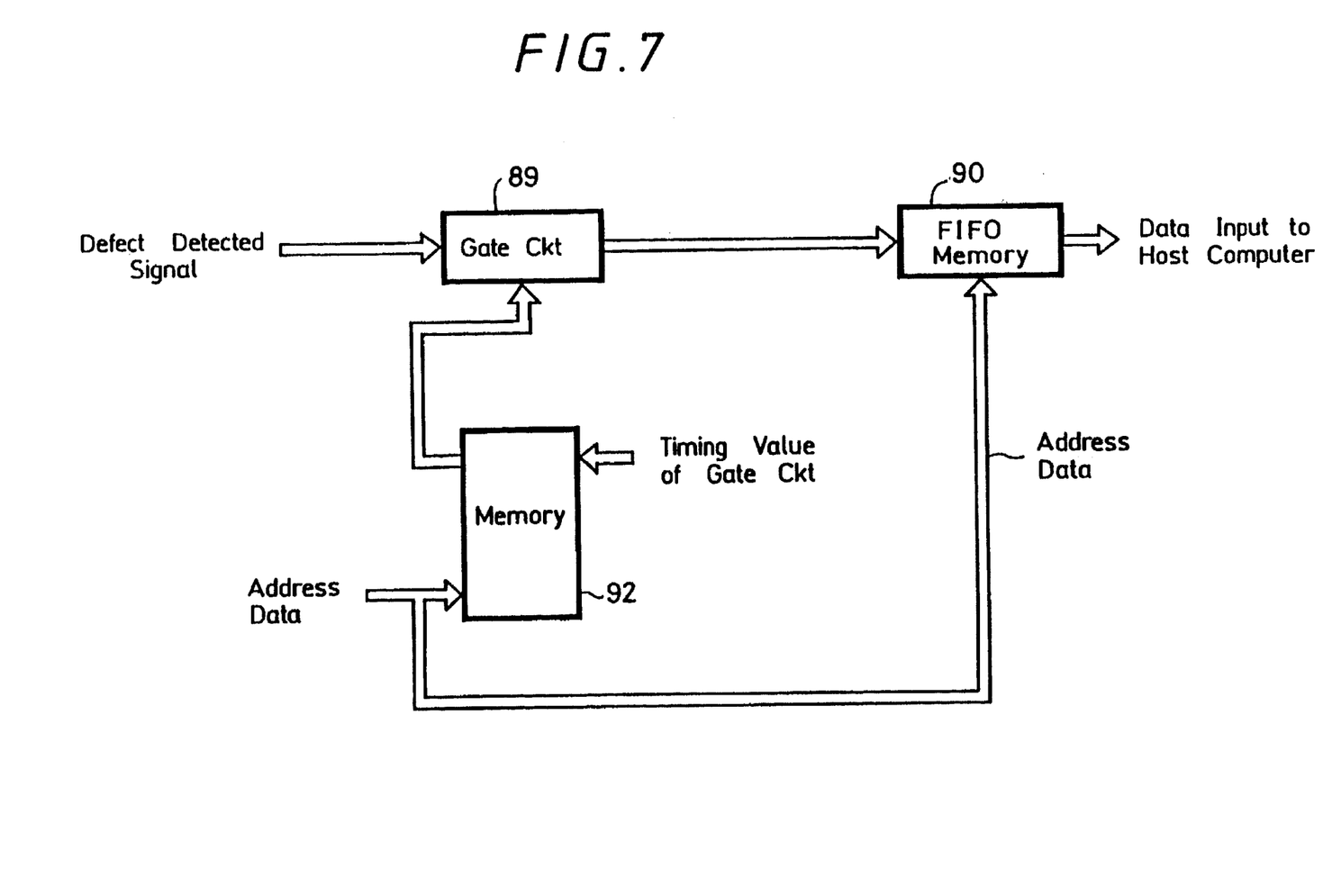
FIG. 7 is a block diagram showing a gate control unit and a defect detected signal output unit according to the embodiment of the present invention.

Arrangements of the defect detectors 82 through 88 shown in FIG. 3 have been described so far. The defect portion detecting unit outputs defect detected signals for every item of detected data supplied to the respective defect detectors 82 to 88. As shown in FIG. 3, defect detected signals output from the defect detectors 82 through 88 are supplied to a gate circuit 89. The address signal from the address generator 81 also is supplied to the gate circuit 89 and the gate circuit 89 can gate the defect detected signal and the address signal by a gate timing signal. The gate timing signal is generated by a memory 92 when the memory 92 compares a gate circuit timing value supplied thereto from the host computer (not shown) and the address signal supplied thereto from the address generator 81 as shown in FIG. 7. In response to the gate timing signal supplied thereto, the gate circuit 89 is operated so as to allow only the detected signals falling in a range (radial position) in which a signal is recorded on an inspected disc to be output therethrough.

A defect detected signal output from the gate circuit 89 and the address signal output from the address generator 81 are supplied to a FIFO memory (first-in first-out memory) 90. The FIFO memory 90 stores the defect detected signals and the address signals indicative of the address positions of the defect detected signals supplied thereto and outputs the defect detected signals and the address signals in the order in which they are stored therein.

The defect detected signals and the address signals output from the FIFO memory 90 are supplied to the host computer (not shown) of the disc defect inspection apparatus. The host computer calculates sizes and areas of defects that occurred in the radial direction and in the circumferential direction from every type of defect detected signals supplied thereto. In this case, the host computer corrects calculated results that fluctuated due to a difference of diameter of the optical disc. Then, the host computer determines the presence or absence of a defect of a predetermined size on the basis of calculated results and determines whether the inspected optical is good or a failure.

As shown in FIG. 3, the host computer (not shown) supplies a mechanism control signal for controlling mechanisms disposed within the inside of the disc defect inspection apparatus through an input/output (I/O) interface circuit 91. Drive mechanisms, such as the spindle motor 2 and the polygon mirror 12 are driven under the control of this mechanism control signal.

According to the disc defect inspection apparatus, since the presence or absence of a defect at each inspection point is detected on the basis of spatial differences among the nearby states of the inspection points, it becomes possible to judge a defect portion with high accuracy. In particular, an ability for judging a defect portion with a low optical contrast can be improved considerably. Even though a defect portion can be inspected with high accuracy, a memory having a relatively small storage capacity for storing data of several scanning lines may be used. Therefore, a disc defect inspection apparatus can be simplified in arrangement.

In the case of this embodiment, since the inspection laser light is distributed in the radial direction of the optical disc by the polygon mirror as parallel scanning lights, the defect portion can be efficiently judged with high accuracy. Specifically, as compared with the case that laser light is spirally scanned along the tracks formed on the optical disc, if the optical disc is rotated once or several times, then the whole surface of the optical disc can be inspected. Therefore, a defect of an optical disc can be inspected accurately and efficiently in a short time period.

In this embodiment, a defect of the optical disc can be detected on the basis of not only the spatial differences among the reference point state and the states of the nearby points of the inspected point (defect portion is detected by the comparator 133 shown in FIG. 4), but also absolute states of respective inspected states (defect portion is detected by the comparator 131). Thus, it is possible to detect a defect of the optical disc more accurately on the basis of both defect inspected results.

In this embodiment, the reflected light intensity, the directly-reflected light intensity, the diffractive index, the complex refractive index, the diffracted light intensity, the radial skew and the tangential skew are inspected individually and thus, the disc state can be inspected more accurately.

While detected data of one scanning line before or after the scanning line of detected data located at the central position are obtained in the outer peripheral side of the optical disc and the data located at the scanning line which precede or succeed the detected data located at the central position of the inner peripheral side by two lines as described above, the present invention is not limited thereto and the number of preceding or succeeding scanning lines may be increased or decreased.

Further, while the signal recording surface of the optical disc is detected as described above, the present invention is not limited thereto and other causes of defect, such as a disc surface state can be inspected.

Furthermore, while the present invention is applied to an inspection apparatus for inspecting a defect of an optical disc having a signal recording surface provided in its inside as described above, the present invention is not limited thereto. It can be applied to an inspection apparatus for inspecting a defect of other disc in and/or from which information is optically recorded and/or reproduced, such as a magneto-optical disc in which data is recorded on a magnetic film by laser light. In addition, the present invention can be applied to an inspection apparatus for inspecting a defect of a disc of a recording system other than the recording system of the disc in which information is optically recorded and/or reproduced.

According to the present invention, it is possible to determine on the basis of reflected light of laser light radiated on the disc whether or not the disc state is normal. In the present invention the disc state can be determined on the basis of compared results of nearby states of respective reflected positions and, thus the disc state can be judged with high accuracy. The memory for storing sensor outputs may store therein only reflected positions and nearby sensor outputs. Therefore, it becomes possible to inspect a defect of a disc with high accuracy by the inspection apparatus having a simple arrangement using memory having a small storage capacity.

Since the sensor outputs are used to detect at least any one of the reflected light intensity, the directly-reflected light intensity, the diffractive index, the complex refractive index, the diffracted light intensity, the radial skew and the tangential skew, it becomes possible to determine whether or not the respective states are proper.

Since laser light that was collimated to parallel scanning light is radiated on the optical disc and laser lights reflected on the optical disc are supplied to the sensors, the inspected portion which may consist of a wide area can be scanned by the parallel scanning laser lights one at a time and the whole of the optical disc can be efficiently inspected. Therefore, it is possible to reduce the time required when one optical disc is inspected.

Further, the sensor outputs of the front and back address positions in the circumferential direction of the optical disc and the sensor outputs of the left and right address positions in the radial direction of the optical disc with respect to the center reference sensor output are used as the nearby sensor outputs. Therefore, the center reference sensor output is compared with the sensor outputs of the front, back, left and right four portions, thereby making it possible to judge a defect of the optical disc more accurately.

Furthermore, the front and back address positions are changed in the circumferential direction of the optical disc depending on the inner and outer peripheral sides of the optical disc so that the distances from the detected position of the center reference sensor output to the detected positions of the sensor outputs of the front and rear address positions are made substantially constant in the inner and outer peripheries of the optical disc. Therefore, it becomes possible to inspect a defect of the optical disc in the inner and outer peripheries of the optical disc under substantially constant conditions.

Having described a preferred embodiment of the invention with reference to the accompanying drawings, it is to be understood that the invention is not limited to that precise embodiment and that various changes and modifications could be effected therein by one skilled in the art without departing from the spirit or scope of the invention as defined in the appended claims.

What is claimed is:

1. An apparatus for inspecting a defect of a disc comprising:

rotating means for rotating said disc;

laser radiating optical means for radiating laser light on said disc rotated by said rotating means, thereby scanning said disc;

sensor for detecting laser light reflected from said disc and outputting an output signal representing said detected laser light;

address generating means for generating address data identifying a respective position on said disc on which said laser light is radiated;

a memory in which output signals of said sensor are written together with said address data in unison with scanning of said laser light; and defect detecting means for detecting a defect on said disc by reading out from said memory a sensor output corresponding to a predetermined disc address position written in said memory and sensor outputs corresponding to disc address positions adjacent to said predetermined disc address position and determining a difference between the sensor outputs corresponding to the nearby positions and the sensor output corresponding to the predetermined address position.

2. An apparatus for inspecting a defect of a disc according to claim 1, wherein said output signal from said sensor represents one of a reflected light intensity, a directly-reflected light intensity, a diffractive index, a complex refractive index, a diffracted light intensity, a radial skew and a tangential skew.

3. An apparatus for inspecting a defect of a disc according to claim 1, wherein said laser radiating optical means includes a laser light source, a polygon mirror for scanning a laser light emitted from said laser light source, and a collimator for collimating said scanned laser light to form parallel scanning light and radiating said parallel scanning light on said disc, and said laser light reflected from said disc is supplied through a condenser lens to said sensor.

4. An apparatus for inspecting a defect of a disc according to claim 1, wherein said sensor outputs corresponding to disc address positions adjacent to said predetermined disc address position are sensor outputs at positions corresponding to front and back address positions in a circumferential direction of said disc relative to a predetermined center reference position and sensor outputs at positions corresponding to left and right address positions in a radial direction of said disc relative to said predetermined center reference position.

5. An apparatus for inspecting a defect of a disc according to claim 4, wherein said front and back address positions in said circumferential direction of said disc are spaced apart from said predetermined center reference position by a predetermined distance at an inner periphery and are spaced apart from said predetermined center reference position by said predetermined distance at an outer periphery of said disc.

* * * * *

UNITED STATES PATENT AND TRADEMARK OFFICE
CERTIFICATE OF CORRECTION

PATENT NO. : 5,646,415
DATED : July 08, 1997
INVENTOR(S) : Yoshitake Yanagisawa

It is certified that error appears in the above-identified patent and that said Letters Patent is hereby corrected as shown below:

Col.1, line 38, change "defect" to --defects--
Col.2, line 51, after "film" insert --,--
Col.3, line 25, change "circular" to --circularly--
Col.4, line 35, after "respectively" insert --,--
       line 41, change "respectively" to --,respectively,--
       line 52, change "respectively" to --,respectively,--
       line 64, change "respectively" first occurrence, to --,respectively,--
       same line, after "respectively" second occurrence, insert --,--
Col.6, line 59, after "respectively" insert --,--
Col.7, line 13, after "respectively" insert --,--
       line 62, after "respectively" insert --,--
Col.8, line 52, after "optical" insert --disc--
Col.9, line 27, after "and" insert --,--
       line 46, change "disc" to --discs--
       line 59, after "thus" insert --,--

<u>In the claims</u>:
Col.10, line 47, before "sensor" insert --a--

Signed and Sealed this

Third Day of March, 1998

*Attest:*

BRUCE LEHMAN

*Attesting Officer*      Commissioner of Patents and Trademarks